United States Patent [19]

Komatsu et al.

[11] Patent Number: 4,612,572
[45] Date of Patent: Sep. 16, 1986

[54] X-RAY TELEVISION DIAGNOSTIC APPARATUS

[75] Inventors: Kenichi Komatsu, Ootawara; Michitaka Honda, Tochigi, both of Japan

[73] Assignee: Tokyo Shibaura Denki Kabushiki Kaisha, Kawasaki, Japan

[21] Appl. No.: 595,440

[22] Filed: Mar. 30, 1984

[30] Foreign Application Priority Data

Mar. 31, 1983 [JP] Japan .................................. 58-56407

[51] Int. Cl.$^4$ .......................... H05G 1/64; H04N 5/34
[52] U.S. Cl. ........................................ 358/111; 378/99
[58] Field of Search ........................ 378/99, 100, 62; 358/110, 111; 128/654

[56] References Cited

U.S. PATENT DOCUMENTS 3,894,181  7/1975  Mistretta et al. .................... 358/111
4,210,812  7/1980  Ando et al. ......................... 250/416
4,355,331  10/1982  Georges et al. .................... 358/111
4,393,402  7/1983  Keyes et al. ....................... 358/111

OTHER PUBLICATIONS

Japanese Patent Disclosure (Kokoku) No. 56-15184.

Primary Examiner—Craig E. Church
Assistant Examiner—Charles F. Wieland
Attorney, Agent, or Firm—Finnegan, Henderson, Farabow, Garrett & Dunner

[57] ABSTRACT

In an X-ray television diagnostic apparatus, the blanking operation of the grid control circuit for the image intensifier and also the scanning operation of the television camera are interrupted during the projection of pulsatory X-rays from the X-ray tube, and at least the blanking operation for the image intensifier commences immediately after the projection of the pulsatory X-rays is accomplished.

7 Claims, 4 Drawing Figures

X-RAY TELEVISION DIAGNOSTIC APPARATUS

BACKGROUND OF THE INVENTION

1. Field of the Invention

The present invention relates to an X-ray television diagnostic apparatus, and more particularly to a diagnostic apparatus for utilizing a fluoroscopy system in which pulsatory X-rays are intermittently projected toward an object under investigation so as to produce X-ray transmission images, the X-ray transmission images of the object are converted by an image intensifier into optical images, the optical images are then converted by a television camera into electric image signals, and thereafter a plurality of electric image signals are processed by the digital time subtraction technique so as to obtain subtracted images of the object, e.g., angiographic images.

2. Description of the Prior Art

Recently "digital radiography" or "digital fluoroscopy" in which a time subtraction and digital processing are utilized has been applied to an X-ray television diagnostic apparatus such that diagnosis utilizing X-rays is performed for circulatory organs, especially an angiographic examination.

The conventional digital fluorography will now be summarized.

First, an X-ray contrast medium is administrated into a predetermined vein of the arm of a patient as an object under investigation. When a given time "TO" has passed after an injection of the X-ray contrast medium, a diagnostic portion of the vein of the patient into which the X-ray contrast medium has not yet been administered, is photographed by an X-ray television camera device at a first X-ray projection. In general, the X-ray television camera device is constructed by an image intensifier, a television camera and an optical system that is optically coupled between the image intensifier and the television camera. An X-ray television signal output from the television camera device is analogue-to-digital converted into a corresponding digital signal. This digital video signal is stored as a mask image data signal in a first digital memory.

When a given time "T1" has passed after the mask image data signal is stored and the X-ray contrast medium is administered, a second X-ray projection is carried out. Subsequently successive X-ray projections are intermittently done at a given timing ratio, e.g., several projections per one minute, so that the diagnostic portion of the patient into which the X-ray contrast medium is flowing, is photographed by the camera device in accordance with a predetermined time lapse. As a result, a series of digital X-ray video signals is stored in turn in a second digital memory as contrast image data signal. Then time subtraction is performed between the mask image data signal in the first memory and the contrast image data signal in the second memory so as to obtain a digital time subtraction image of the object.

The resultant subtraction image signal in digital form is converted by an A/D converter so as to obtain an analogue subtraction image signal, whereby it is displayed on a monitor screen, or converted by a multi-format camera to obtain a film image. On the other hand, the digital filtering process is executed by utilizing a plurality of X-ray television signals with respect to a time lapse, so that a differential image, low-pass-filtered or high-pass-filtered image is displayed on the monitor screen.

In such a diagnostic apparatus as here set forth, pulsatory X-rays are employed in order to reduce the total quantity of the X-ray projection received by the object. On the other hand, there are the following problems due to afterimage phenomenon on the image intensifier. That is, when an X-ray control pulse is generated synchronized with the field sync pulse of the television camera, an optical (fluorescent) image is output from the image intensifier. This optical image has a waveform in that its leading edge raises sharply, and its trailing edge falls gradually in phase with the trailing edge of the X-ray control pulse. If the scanning operation of the television camera commences immediately after the trailing edge of the X-ray control pulse, a fluctuation of the brightness may occure in the upper and lower regions of the monitor screen because the leading edge of the optical image functions as the afterimage.

To mitigate a above-mentioned drawbacks, the known apparatus has been proposed in, e.g., Japanese Patent Publication No. 56-15184(1981). According to this known apparatus, the blanking signal is applied to the television camera during a time period from the leading edge of the optical image to the disappearance thereof. In other words, during a period defined by adding one sync field period to the afterimage period, the scanning operation of the television camera is blanked out. After such a long blanking period, the scanning operation commences, so as to obtain an X-ray television signal.

There is, however, the other problem that the camera blanking period is susceptible to both the duration time of the X-ray control pulse and the characteristics of the image intensifier. Namely it may not be precisely determined. If the disappearance of this afterimage phenomenon takes a long time (involving several field sync pulse signals), it is therefore required to set a long blanking period. As a result, the scanning operation of the television camera must be delayed for a relatively long time after the X-ray projection is accomplished, so that due to such a long time interval between the successive X-ray projections, available frame numbers per unity time are reduced. Accordingly the resultant image signals cannot precisely indicate the portion under examination having a fast movement.

Moreover since the blanking period of the television camera cannot be assigned to a given period and thus the various timing signals for the write/read signals, scanning of the television camera, and the X-ray projection control signal do not have constant values, there exist drawbacks that the synchronization circuit becomes complex and the production cost of the entire system is expensive.

It is therefore an object of the present invention to provide an X-ray television diagnostic apparatus in which precise X-ray transmission images are available without the adverse influence by the inherent afterimage phenomenon of the image intensifier.

It is another object to provide an X-ray television diagnostic apparatus in which the scanning timing of X-ray transmission images through the image intensifier by the television camera can be precisely determined in synchronization with the field sync pulse signal, and also the X-ray projection intervals can be shortened.

SUMMARY OF THE INVENTION

These objects and features of the present invention may be realized by providing an X-ray television diagnostic apparatus comprising:

a source for generating a pulsatory X-ray;

image intensifying means which receives an X-ray transmission image of an object under investigation that is produced by a penetration of the pulsatory X-ray through the object, and which produces an optical image of the object;

television camera means;

an optical system optically-coupled between the image intensifying means and the television camera means which transfers the optical image from the image intensifying means to the television camera means;

light interrupting means provided in at least one of the image intensifying means and the optical system so as to interrupt the transfer of the optical image to the television camera means;

A/D converting means for converting an analogue image signal that is derived from the television camera means into a corresponding digital image signal;

storage means which includes at least first and second frame memories, and stores the digital image signal from the A/D converting means;

algorithmic means which performs given image processing for at least two sets of the digital image signals that are previously stored in the first and second frame memories respectively so as to derive an image-processed digital signal;

D/A converting means for converting the image-processed digital signal into a corresponding imageprocessed analogue signal;

monitor means for displaying the image-processed analogue signal from the D/A converting means;

pulse generating means for generating pulse signals that are adapted to the television camera means as field sync pulse signals;

camera control means for controlling at least scanning of the optical image which is incident upon the television camera means;

optical blanking control means for controlling the blanking timing operation of the light interrupting means;

X-ray control means for controlling a projection of the pulsatory X-ray from the pulsatory X-ray generating source, and system control means which performs controls of the apparatus in such a manner that the projection of the pulsatory X-ray toward the object commences in synchronized with the field sync pulse signals under the control of the X-ray control means, the blanking operation of the light interrupting means is interrupted and the scanning operation of the television camera means is blanked out under the control of the optical blanking control means and the camera control means respectively while the projection of the pulsatory X-ray is continued, and at least the blanking operation of the light interrupting means commences immediately after the projection of the pulsatory X-ray is accomplished.

Further, they may be obtained by providing an X-ray television diagnostic apparatus comprising:

a first source for generating a first pulsatory X-ray;

first image intensifying means which receives a first X-ray transmission image of an object under investigation that is produced by a penetration of the first pulsatory X-ray through the object, and which produces a first optical image of the object;

first television camera means;

a first optical system optically-coupled between the first image intensifying means and the first television camera means, which includes at least first light interrupting means, and transfers the first optical image from the first image intensifying means to the first television camera means;

a second source for generating a second pulsatory X-ray;

second image intensifying means which is positioned at a given angle with respect to the first image intensifying means, receives an X-ray transmission image of the object under investigation that is produced by a penetration of the second pulsatory X-ray through the object, and produces a second optical image of the object;

second television camera means;

a second optical system optically-coupled between the second image intensifying means and the second television camera means, which includes at least second light interrupting means, and transfers the second optical image from the second image intensifying means to the second television camera means;

video selecting means for selecting first and second analogue image signals that are alternately derived from the first and second television camera means respectively;

A/D converting means for converting the first and second analogue image signals into first and second digital image signals, respectively;

store means which includes at least first and second frame memories and stores therein the first and second digital image signals from the A/D converting means, respectively;

Algorithmic means which performs given image processing for at least two sets of each of the first and second digital image signals independently that are previously stored in the first and second frame memories respectively so as to derive first and second image-processed digital signals;

D/A converting means for converting the first and second image-processed digital signals into first and second analogue image signals respectively;

monitor means for displaying the first and second image-processed analogue image signals from the D/A converting means;

pulse generating means for generating pulse signals that are adapted to the first and second television camera means as field sync pulse signals;

first camera control means for controlling at least scanning of the first optical image which is incident upon the first television camera means;

first optical blanking control means for controlling the blanking timing operation of the first light interrupting means in the first optical system;

second camera control means for controlling at least scanning of the second optical image which is incident upon the second television camera means;

second optical blanking control means for controlling the blanking timing operation of the second light interrupting means in the second optical system;

X-ray control means for controlling projections of the first and second pulsatory X-rays from the first and second pulsatory X-ray generating sources; and system control means which performs controls of the apparatus in such a manner that the projection of the first pulsatory X-ray toward the object commences, prior to that of the second pulsatory X-ray, in synchronized with the field sync pulse signals under the control of the X-ray control means, the scanning operations of the first and second television camera means are blanked out under the control of the first and second camera control means, respectively and the blanking operation of the second optical interrupting means is carried out under the control of the second optical blanking control means while the projection of the first pulsatory X-ray is continued, and at least the blanking operation of the first light interrupting means commences immediately after the projection of the pulsatory X-ray is accomplished.

BRIEF DESCRIPTION OF THE DRAWINGS

The present invention is best understood with reference to the accompanying drawings, in which.

DETAILED DESCRIPTION OF THE PREFERRED EMBODIMENTS

Before proceeding with the various types of the preferred embodiments, a fundamental operation of the X-ray television diagnostic apparatus in accordance with the present invention will now be explained.

That is, the pulsatory X-rays are intermittently projected toward the object under examination. Optical (fluorescent) images of the object are produced by an image intensifier onto which the X-ray transmission images of the object are incident. The optical images are scanned by a television camera so as to produce video image signals of the object under examination. Those video image signals are processed in the digital time subtraction method, so that subtraction images of the object may be obtained. The present invention has a feature such that during the X-ray projection toward the object, the scanning operation by the television camera is blanked out, the optical image production by the image intensifier is blanked out in synchronously with the control pulse for the X-ray projection, and both the control signal and scanning timing are synchronized with the field sync pulse signal of the television camera.

Figure 1:
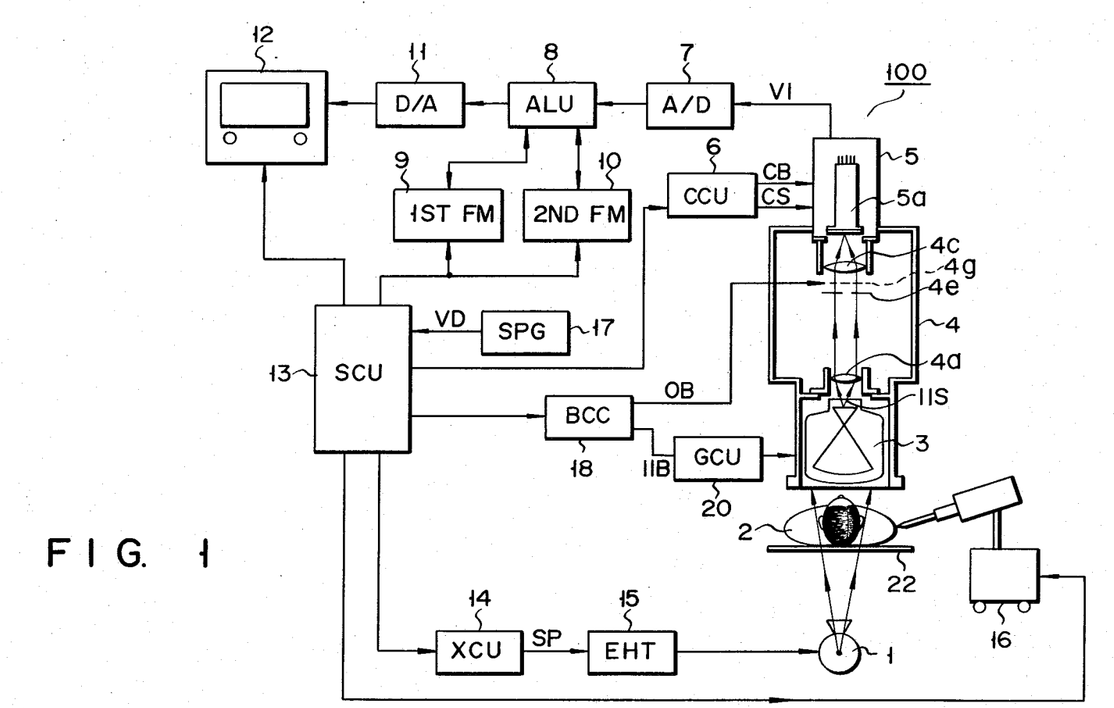
FIG. 1 schematically shows a block diagram of an X-ray television diagnostic apparatus according to one preferred embodiment.

FIG. 1 shows a block diagram of an X-ray diagnostic apparatus 100 as one preferred embodiment according to the invention.

Reference numeral 1 denotes an X-ray tube for projecting pulsatory X-rays toward an object 2, e.g., a patient. Reference numeral 3 indicates an image intensifier upon which X-ray transmission images produced by the pulsatory X-rays are incident, and which converts those pulsatory X-ray transmission images into optical (fluorescent) images. Reference numeral 4 denotes an optical system. The optical system 4 is constructed by a primary lens 4a that is positioned in front of the output end of the image intensifier 3, a secondary lens 4c that is positioned in front of a pick-up tube 5a of an X-ray television camera 5 (simply referred to as "television camera"), an auto-iris 4e which is positioned between the primary and secondary lenses 4a and 4c and which automatically controls the amount of light of the optical image incident upon the secondary lens 4c, and an auto-shutter element 4g such as a liquid crystal shutter which automatically interrupts a transfer of the optical image to the pick-up tube 5a of the television camera 5. As will be described in detail later, the optical system 4 has a function that the optical image derived from the image intensifier 3 is optically transferred into the television camera 5.

The pick-up tube 5a of the television camera 5 may employ various types of tubes, e.g., vidicon, plumbicon, silicon-vidicon, Newbicon (trade name) Saticon (trade name), Chalnicon (trade name). In particular, it is preferable to employ such a pick-up tube whose photoconductive plate is made of PbO (lead monoxide), because of its sharp response characteristic.

Reference numeral 6 denotes a television camera control unit (referred to as "camera control unit"). The camera control unit 6 generates at least a blanking control signal CB by which the scanning operation of the television camera can be blanked out. An A/D converter 7 is connected to the television camera 5 to A/D convert the video (image) signal VI into a corresponding digital video signal. An algorithmic unit 8 is connected to the A/D converter 7 to receive the digital video signal VI. The function of the algorithmic unit 8 is as follows. A series of the digital video signals VI is alternately stored in a first frame memory 9 as a first image data signal and a second frame memory 10 as a second image data signal, and image processing such as a digital time subtraction is carried out for the first and second image data signals so as to obtain an image-processed (,e.g. subtraction) image signal.

A D/A converter 11 is connected to the algorithmic unit 8 so as to D/A-convert the image-processed image signal in a digital form into a corresponding image signal in an analogue form. A monitor 12 is connected to the D/A converter 11 so as to display an image of the image-processed image signal. A system control unit 13 is provided to control the above-described camera control unit 6, frame memories 9 and 10, the monitor 12 and so on. A detailed description of the functions of the system control unit 13 will be made later. An X-ray control unit 14 is controlled by this system control unit 13 so as to apply an X-ray control (pulse) signal SP to an extra high-tension unit 15 that drives an X-ray tube 1. An injector 16 is connected to the system control unit 13 so as to administrate an X-ray contrast medium into the object 2, i.e., blood vessels of the patient. This injector 16 is comprised of syringes for injecting the contrast medium and a device for driving those syringes. The injection timing of the contrast medium is automatically controlled by the system control unit 13.

Furthermore a sync pulse generator 17 is provided to generate field sync pulse signals VD for the television camera 6. Those field sync pulse signals VD are used as reference signals for the system control unit 13 and timing signals for driving the monitor 12 and the injector 16. Based upon the field sync pulse signals, all of the circuits employed in this apparatus 100 can be controlled through the system control unit 13.

An optical blanking control circuit 18 is coupled to the image intensifier 3 so as to selectively produce one blanking signal IIB for the image intensifier 3 and another blanking signal OB for the optical system 4, i.e., the auto-shutter 4g. That is, blanking signals IIB and OB are to optically interrupt transfer of the optical image of the ojbect 2 from the image intensifier 3 to the television camera 5. For example, the blanking signal IIB is applied to a grid control unit 20 which is provided in the image intensifier 3. The blanking operation of the grid control unit 20 is carried out in such a manner that the operation of the image intensifier 3 is blanked out only during a low level of the blanking signal IIB.

Figure 2:
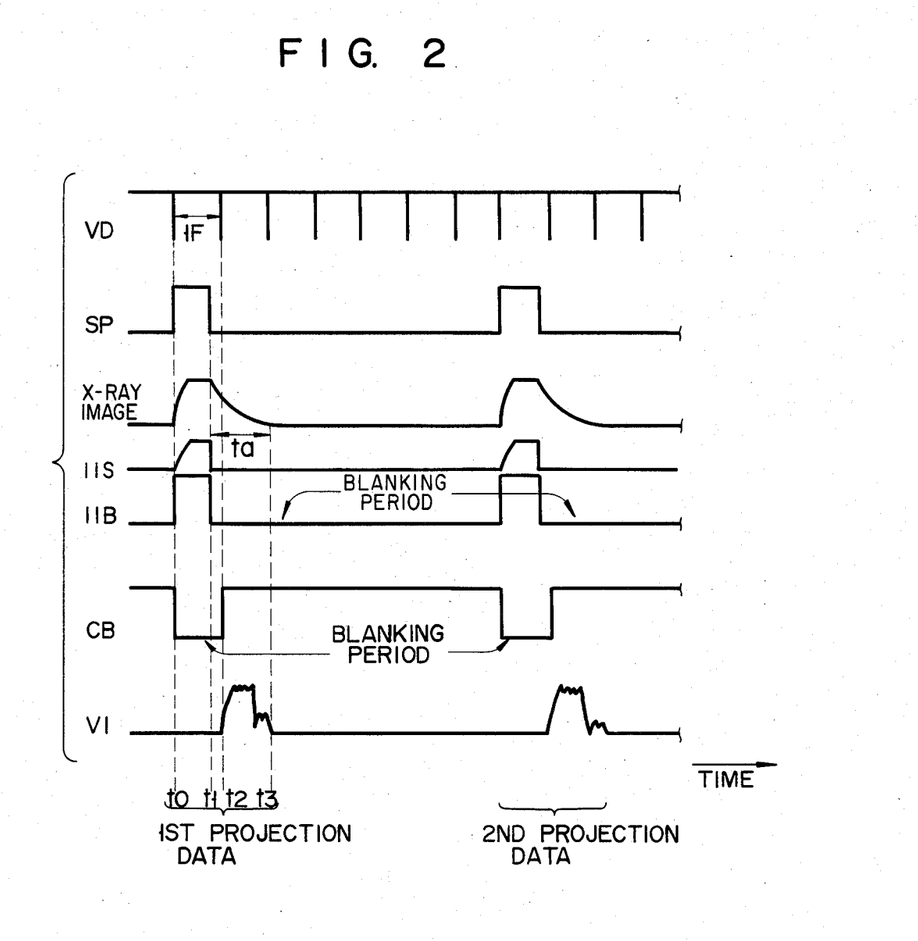
FIG. 2 is a timing chart of waveforms of major circuit elements employed in the apparatus shown in FIG. 1.

Before proceeding with the operation of the X-ray television diagnostic apparatus 100, signal waveforms shown in FIG. 2 will now be explained in detail.

The field sync pulse signal of the television camera 5 is denoted by the symbol "VD". This pulse signal VD is generated in the sync pulse generator 17. The X-ray control signal (control pulse signal) is indicated by the symbol "SP". The X-ray control signal SP is produced from the X-ray control unit 14 in synchronized with the field sync pulse VD, and has its pulse width which is approximately $\frac{2}{3}$ of that of the field sync pulse VD. That is, the duration time period of this signal SP (t0-t1) is about $\frac{2}{3}$ of that of one field sync period. The optical image output of the image intensifier 3 is indicated by the symbol "IIS". As seen from the time chart of FIG. 2, there still remains an afterimage for a time period "ta" after the trailing edge of the X-ray control pulse signal SP. The blanking signal for the image intensifier 3 is indicated by the symbol "IIB", which is the same as the X-ray control signal SP in its phase. When this blanking signal IIB becomes a low level, the operation of the image intensifier 3 is blanked out so that no optical image is output from the image intensifier 3. The blanking signal IIB is generated in the optical blanking control circuit 18. Another blanking signal is denoted by the symbol "CB" and is generated in the television camera control circuit 6. The blanking period of the blanking signal IIB is equal to one field sync period in this embodiment. During this blanking period the level of the blanking signal becomes low. The video signal of the television camera 5 is indicated by the symbol "VI".

The operation of the diagnostic apparatus 100 will now be described with reference to FIGS. 1 and 2.

After the patient 2 is conducted to lie on the couch 22, a start button (not shown) is depressed under the predetermined photographic conditions. Then an injection of X-ray contrast medium commences from the injector for X-ray contrast medium 16. After a given time has passed from this injection, the X-ray control pulse SP is derived at an instant "t0" from the X-ray control unit 14 synchronized with the field sync pulse VD, so that a first pulsatory X-ray is projected from the X-ray tube 1 so as to obtain a mask image of the patient 2. Accordingly the X-ray which has penetrated through the patient 2 is incident upon the input fluorescent face of the image intensifier 3 as an X-ray transmission image of the patient 2, so that it is converted into an optical (fluorescent) image IIS. The intensity characteristic of this optical image IIS is shown in FIG. 2. That is, the outline of this image intensity is such that the intensity of the optical image becomes rapidly large at the instant "t0" (start of the X-ray projection), thereafter saturates (t0~t1), and gradually declines (t1-t3) after the X-ray projection is completed. A portion of the optical image (instants t1 to t3) is so-called as an afterimage of the optical image. A period of the afterimage is indicated by "ta". In general, it is known that an occurence of this afterimage is caused by the cable capacitance of the high-tension cable for the X-ray tube.

As the level of the blanking signal IIB for the image intensifier 3 is kept high during the X-ray projection (instants "t0" to "t1"), the optical blanking operation for the image intensifier 3 is interrupted, so that the optical image is incident upon the target of the pick-up tube 5a in the television camera 5 via the optical system 4, and thus a storage of the optical image is carried out therein (during this time period, the scanning of the television camera 5 is blanked out). At the time instant "t1", the X-ray projection is completed and the blanking signal IIB becomes low. As a result, the optical image can be output no longer from the image intensifier 3. In other words, a portion of the optical image which is called as "the afterimage" is optically blanked out in the image intensifier 3. Under such operations, the optical (fluorescent) image is available and can be stored in the target of the pick-up tube 5a during only the time period from "t0" to "t1" (a generation of the X-ray control pulse SP). However since the scanning operation of the television camera 5 is blanked out by the electrical blanking signal CB for the time period from "t0" to "t2" (corresponding to one field sync period "1F"), no optical image is generated from the target stored by the pick-up tube 5a during time t0 through t2. This time period (t0-t2) is longer than that of the X-ray control signal Sp. If the scanning operation of the television camera 5 would not be blanked out, the brightness of the read video signal VI would change in the vertical direction of the monitor screen. After the time instant "t2", the signal level of the blanking signal for television camera CB becomes high, so that the scanning of the television camera 5 commences, and the optical image which has been stored during the above-described period "t0" to "t1" is read out as an electric image signal, thus deriving the video signal VI.

Consequently, even if the time period "ta (instants t1-t3)" of the afterimage exceeds one field sync period, such an optical image (afterimage) can be completedly cut out by the optical blanking signal IIB preventing its transferrence via the optical system 4 to the target of the pick-up tube 5a. Since, according to the present invention, this afterimage gives no adverse effect to the video signal VD, the scanning of the television camera 5 can be performed synchronized with the field sync pulse signal VD. The video signal VD relating to the first pulsatory X-ray is analogue-to-digital converted into the digital video signal by the A/D converter 7, and then applied to the algorithmic unit 8. It is stored into the first frame memory 9 as the mask image data signal.

Then the second pulsatory X-ray is generated and projected toward the patient 2 into which the X-ray contrast medium has been administrated. The video signal VI relating to the second pulsatory X-ray can be obtained in the same manner as in the first pulsatory X-ray without the adverse effect by the afterimage. This video signal VI is stored through the A/D converter 7 and the algorithmic unit 8 into the second frame memory 10 as the first contrast image data signal.

Thereafter the mask image data signal and the first contrast image data signal that have been stored in the first and second frame memories respectively are sent into the algorithmic unit 8, and are time-subtracted therein. The subtraction image signal in the digital form is converted by the D/A converter 11 and then diplayed in the monitor 12 as a first subtraction image of the patient 2.

Afer the above-described second X-ray projection is accomplished, the succeeding X-ray projections, e.g., a third X-ray projection are carried out in turn in the same operation as the first and second X-ray projections so as to obtain subsequently second and third contrast images. The digital time subtraction is furthermore performed between those contrast image data signals and the mask image data signal so that second and third subtraction images are sequentially obtained. For clarity, the timing chart of FIG. 2 shows only first and second projection data.

In accordance with the first embodiment described above, since the blanking operation of the image intensifier 3 can start immediately after the X-ray projection is accomplished, namely when the occurrence of the afterimage of the optical image begins, it is possible to obtain the digital subtraction image signals which are not influenced by the afterimage of the optical image.

Accordingly since the time interval between successive X-ray projections can be shortened, there is an advantage to utilize the diagnostic apparatus 100 in the diagnosis of fast-moving diseased portions under examination, e.g., the angiography for the coronary arteries.

Furthermore, as the scanning timing of the television camera 5 can be synchronized with the field sync pulses, a commercially available television system can be used in the diagnostic apparatus 100. As a result, a compact, low-cost and light-weight apparatus can be realized because no specifically designed system is required.

A second preferred embodiment will now be described with reference to FIGS. 3 and 4. It should be noted that the same reference numerals shown in FIGS. 1 and 2 will be employed as those for denoting the same circuit elements shown in the following figures.

Particularly the X-ray television diagnostic apparatus 200 according to this embodiment is suitable to be utilized in the field of the bi-plane type angiography on, for example the coronary arteries of the heart, or the arteries of the brain.

Figure 3:
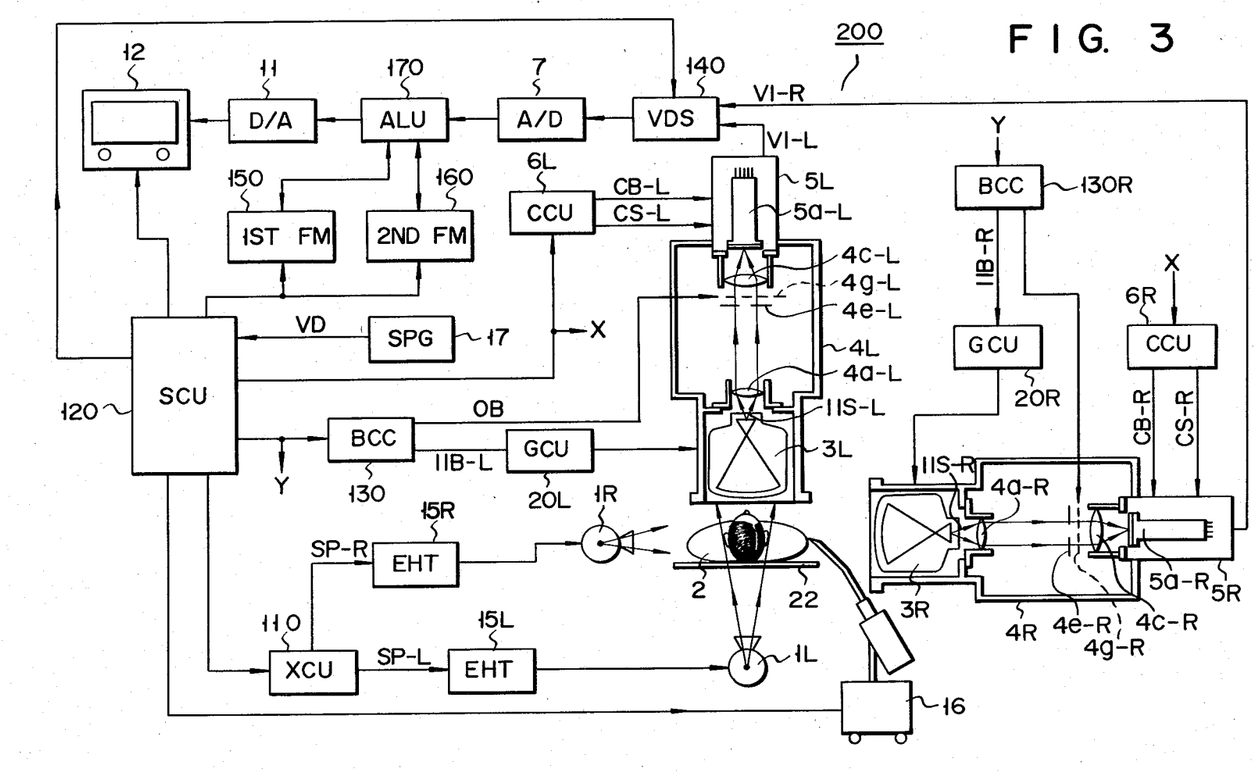
FIG. 3 schematically shows a block diagram of an X-ray television diagnostic apparatus according to another preferred embodiment.
Figure 4:
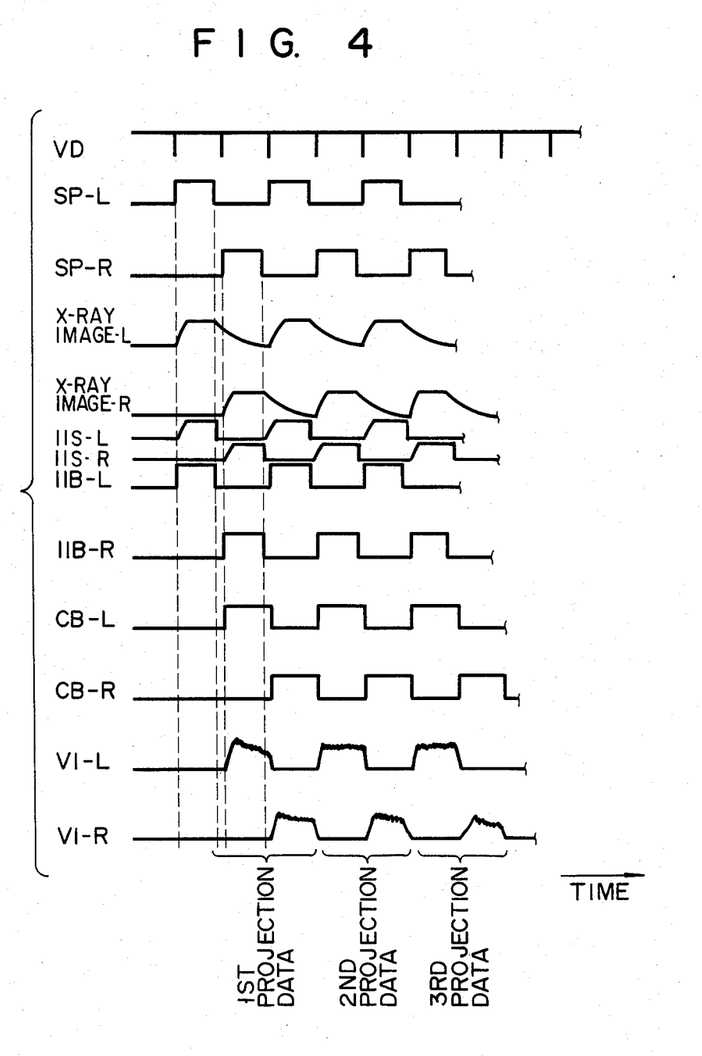
FIG. 4 is a timing chart of waveforms of major circuit elements employed in the apparatus shown in FIG. 3.

In the entire system shown in FIG. 3, an X-ray source and an X-ray photographing arrangement are arranged in a front direction with respect to the patient 2. This photographing arrangement is called "a left photographing arrangement" in this embodiment. Furthermore another X-ray source and X-ray photographing arrangement are arranged in a side direction with respect to the patient 2, i.e., in a direction perpendicular to the front direction. This photographing arrangement is called "a right photographing arrangement" in this embodiment.

Two sets of the X-ray tubes 1L and 1R are disposed in such a manner that the X-ray projection from the left X-ray tube 1L directed toward the back of the patient 2 and that from the right X-ray tube 1R is directed toward the left arm of the patient 2, i.e., the tube 1L being positioned normal to the tube 1R (see FIG. 3). X-ray tubes 1L and 1R are connected via respective extra high-tension units 15L and 15R to an X-ray control unit 110. As will be described in detail later, a pulsatory X-ray is alternately projected from the tubes 1L and 1R at a given timing under the control of the X-ray control unit 110. This alternating X-ray projection can be controlled based upon a control signal derived from a system control unit 120.

Left and right optical blanking control circuits 130L and 130R are respectively connected to the system control unit 120. Grid control units 20L and 20R, or auto-shutters 4g-L and 4g-R are selectively controlled by the left and right optical blanking control circuits 130L and 130R respectively, so that optical paths of the optical systems 4L and 4R, or optical function of the image intensifiers 3L and 3R are selectively interrupted so as not to transfer or intensify the optical images incident on the left image intensifier/optical system, or the right image intensifier/optical system to left and right television cameras 5L and 5R (i.e., targets of the left and right pick-up tubes 5a-L and 5a-R), respectively. That is, the right image intensifier 3R is electrically connected via the right grid control circuit 20R to the right optical blanking control circuit 130R. As the arrangement of the left photographing arrangement is the same as that of the first embodiment, an explanation thereof will be omitted.

Left and right camera control units 6L and 6R are connected to the system control unit 120, thereby alternatively controlling the scanning operations of the left and right television cameras 5L and 5R.

The typical operation of the bi-plane angiography will now be described as a second embodiment with reference to the waveforms shown in FIG. 4.

As same as in the first embodiment, the field sync pulse signal VD is generated as a reference signal from the sync pulse generator 17. This field sync pulse signal VD is applied to the system control unit 120. In this system control unit 120, timing control signals for various circuit arrangements in the diagnostic apparatus 200 are produced based upon the field sync pulse VD.

First, to obtain the mask image signals of the patient 2, the timing control signal is applied to the X-ray control unit 110 from the system control unit 120. As shown in the waveforms of FIG. 4, the projection control signal SP-L is applied to the left extra high-tension unit 15L so as to first energize the left X-ray tube 1L in synchronized with the field sync pulse signal VD. While this projection control signal SP-L is applied (,i.e., the duration time thereof), the blanking signal IIB-L is supplied to the grid control circuit 20L of the left image intensifier 3L so as to introduce the X-ray transmission image of the patient 2 into the image intensifier 3L. As a result, the left optical image IIS-L is derived from the output of the image intensifier 3L (see FIG. 4). It is obvious that the phenomenon of the afterimage of the optical image will surely occur. On the other hand, while this X-ray projection is continued, the scanning operation of the left television camera 5L is required to be blanked out and simultaneously the blanking operations for both the right television camera 5R and the image intensifier 3R should be performed. Otherwise, there is a problem that unwanted optical image is stored on the targets of the pick-up tubes 5a-L and 5a-R of the left and right television camera 5L and 5R.

Immediately after the first X-ray projection is accomplished, the blanking signal IIB-L (a low level) is applied to the grid control unit 20L for the left image intensifier 3L from the blanking control circuit 130, so that the blanking operation of the image intensifier 3L can commence and the scanning operation of the television camera 5L can start in synchronized with the succeeding field sync signals by releasing the blanking operation of the television camera 5L (precisely speaking, this scanning is controlled by the signal CS-L from the camera control unit 6L). Accordingly the left video signal VI-L is derived from the television camera 5L and then applied to one input of a video selector 140.

While the scanning operation of the video signal VI-L for the left side of the patient 2 (actually a front view of the patient 2) is continued, the X-ray projection for the right side of the patient 2 can be performed. In other words, the left grid control unit 20 has been brought into the blanking operation during this scanning period of the left video signal VI-L.

In accordance with the similar operations, the successive X-ray projections and scanning operations can be effected as shown in the waveforms of SP-L and SP-R in the predetermined sequence. As a result, the left and right video signals VI-L and VI-R are alternately applied to the two inputs of the video selector 140 from the left and right television cameras 5L and 5R respectively. Those signals are converted by the A/D converter 7 into corresponding digital video signals and thereafter stored in the first frame memory 150. That is, the left and right video signals which are taken before injections of the X-ray contrast medium into the desired portion of the patient 2, are stored in the first frame memory 150 as the left and right mask image data signals. Accordingly the capacity of the first frame memory 150 is twice as that of the first frame memory 9.

Further, the left and right video signals are stored as the first contrast image data signals in the second frame memory 160. Those video signals are obtained by projecting the pulsatory X-rays toward the object at the given time intervals after the injection of the X-ray contrast medium.

When the four X-ray projections have been completed, the left/right mask image data signals, and the left/right contrast image data signals are stored in each of the first and second frame memories 150 and 160. Next, the predetermined time subtraction is carried out under the control of the algorithmic unit 170 between those mask image data signals and also corresponding contrast image data signals independently. That is, for example, the left mask image data signal is subtracted by the left contrast image data signal so as to obtain a digitial subtraction image signal for the left side of the patient 2. Accordingly those digital subtraction image signals are converted by the D/A converter 11 and then displayed on the monitor 12 subsequently.

After the above-described projection data aquisition, a second contrast image signal and a third contrast image signal are obtained in turn by continuing the projections of the pulsatory X-rays. These image signals are stored in the second frame memory 160 by subsequently refreshing the memory contents thereof before each storage operation. A further digital subtraction is effected between the mask image data signal and each of those contrast image data signals. For example, a digital subtraction is performed between the data signal of the right mask image which is stored in the first frame memory 150 and the data signal of the third right contrast image which is stored in the second frame memory 160 so as to obtain the third subtraction image of the patient 2.

As previously described in detail, the video signals having different diagnostic information on the same patient under examination can be selectively obtained by projecting the pulsatory X-rays toward the patient at different projection angles in accordance with the second preferred embodiment. Accordingly the X-ray television diagnostic apparatus 200 is especially suitable to angiographic diagnosis for the blood vessels, such as the coronary artries of the heart that are positioned in a three dimensional plane. In other words, it is required to excecute such a bi-plane diagnosis that both the scanning operation of the television camera and the optical system including the image intensifier are blanked out simultaneously by employing the diagnostic apparatus as shown in FIG. 2.

While the present invention has been described using a specific embodiment, it should be understood that further modifications, changes and omissions can be made without departing from the scope of the present invention.

For example, in the first and second embodiments, the pulse width of the X-ray projection control signal is selected to have $\frac{2}{3}$ width of one field sync pulse. It is possible to select a pulse width exceeding that of one field sync pulse, or a pulse width shorter than the above $\frac{2}{3}$ width. Anyhow if the leading edge of the projection control signal is synchronized with that of the field sync pulse, it is possible to determine arbitarily the pulse width of the control signal.

In the previous embodiments, a control signal for interrupting the X-ray transmission image is the grid control signal which is derived from the optical blanking control signal. Alternatively a control signal "OB" may be employed to control the auto-shutter 4g assembled in the optical system. Moreover it is possible to utilize both control signals for an interruption of the transfer of the optical image. In these cases, it is designed that the blanking control signal for the auto-shutter has the same repetition frequency as that for the grid of the image intensifier and its reversed polarity with respect to that for the grid. As a result, when the blanking control signal for the auto-shutter becomes a high level, the blanking operation by the auto-shutter is carried out for the incident optical image in the optical system.

In accordance with the invention, the X-ray television diagnostic apparatus may be also used in such a condition that the duration time period of the afterimage on the image intensifier exceeds over one field sync period. In this case, it is required to extend the blanking period for the television camera to an end of such a field sync period belonging to the trailing edge of the X-ray projection control signal. That is, the camera blanking period is set in such a manner that it is equal to a period defined by multiplying 1 field sync period by a given integer. There is an advantage that such a longer camera blanking period is suitable for the angiography of the slow movement object.

It is also possible to employ more than three pieces of the frame memories as the memory means. For example, the second contrast image may be stored in the third frame memory.

In the previous embodiments the digital time subtraction is carried out as the image processing, but a filtering process may be alternatively introduced. Furthermore the so-called "Time Interval Difference" subtraction method may be employed.

It is obvious that both the data storage operation to the frame memories as well as the display operation of the subtraction images to the monitor are not restricted to those in the above-mentioned embodiments. For example, dividing the monitor screen into two regions enables the left and right subtraction images to be simultaneously displayed.

Two sets of TV monitors may be employed, i.e., one for displaying the left subtraction image, and the other for displaying the right subtraction image.

In the previous embodiment, the video selector is connected to receive the analogue video signals from the television camera alternately. It is also possible to connect it to the output of the A/D converter so as to receive the digital video signals therefrom. As a result, the S/N ratio can be improved.

What is claimed is:

1. An X-ray television diagnostic apparatus for examining an object, comprising:
   a source for generating pulsatory X-rays delivered to the object to produce pulsed X-ray images;
   visible imaging means for receiving said pulsatory X-ray images and converting said X-ray images to corresponding optical images;
   television means, including a television camera operating at a predetermined field rate and having a target that is scanned, for producing analog video signals representative of said optical images stored in said target;
   synchronizing generating means for generating field synchronizing signals at the field rate of said television camera;
   exposure control means responsive to said field synchronizing signals for generating X-ray control signals so as to cause said source to emit said pulsatory X-rays with a predetermined exposure time;
   visible imaging control means for generating image blanking signals for said visible imaging means so as to cause said corresponding optical image to be delivered to said television means only during emission of said X-rays by said X-ray source;
   television control means for generating field blanking signals relative to said X-ray control signals so as to cause said television means to be blanked out during emission of said X-rays by said X-ray source;
   memory means for storing said analog video signals from said television means;
   subtracting means for producing analog difference video signals corresponding to a subtraction between analog video signals recently supplied by said television means and analog video signals previously stored in said memory means; and
   display means for producing visible difference video signals.

2. An apparatus as claimed in claim 12, wherein said visible imaging means includes a grid control circuit connected to the visible imaging control means for receiving said image blanking signals, and
   said visible imaging control means controls the visible imaging means in such a manner that immediately after emmission of each one of the pulsatory X-rays, the grid control circuit causes blanking of said corresponding optical images.

3. An apparatus as claimed in claim 2, further comprising:
   injector means for administering an X-ray contrast medium into the object in response to the field synchronizing signals.

4. An apparatus as claimed in claim 1, wherein said visible imaging means includes an auto-shutter connected to receive image blanking signals from said visible imaging control means, and
   the visible imaging control means controls the visible imaging means in such a manner that immediately after each of the pulsatory X-rays have been emitted, the blanking operation of the auto-shutter commences.

5. An X-ray television diagnostic apparatus for examining an object, comprising:
   first and second means for producing analog video signals representative of an optical image corresponding to a pulsed X-ray image of the object,
   said first and second means each including a respective X-ray source for generating pulsatory X-rays delivered to the object, an imaging intensifier for receiving said X-rays transmitted through the object and for converting said transmitted X-rays to corresponding optical images, and a television camera operating at a predetermined field rate for producing analog video signals representative of said optical images, and
   said first and second means being disposed relative to the object at two different angles so as to obtain X-ray images of the object in different directions;
   synchronizing generating means for generating field synchronizing signals at the field rate of said television camera;
   memory means coupled to said first and second means for storing said analog video signals supplied from said respective television cameras;
   subtracting means for producing analog difference video signals by performing a subtraction between analog video signals currently supplied by said first and second means and preceding video signals previously stored in said memory means;
   display means for producing visible difference images corresponding to said analog difference video signals; and
   system control means coupled to said first and second means for generating (1) control signals relative to said field synchronizing signals so as to cause said X-ray sources alternately to emit said pulsatory X-rays with a predetermined exposure time, (2) image blanking signals responsive to said control signals so as to cause the imaging intensifier of the respective one of said first and second means whose X-ray source is being activated to produce said corresponding optical images only during the emission of X-rays from said X-ray source, and (3) field blanking signals responsive to said image blanking signals so as to cause the television camera of the respective one of said first and second means whose X-ray source is being activated to be blanked out during emission of said X-rays wherein said camera has a target for storing said optical images.

6. An apparatus as claimed in claim 5, wherein each imaging intensifier of said first and second means comprises a grid control circuit connected to an optical blanking control means receiving said image blanking signals for controlling the respective imaging intensifier in such a manner that immediately after the pulsatory X-rays from the respective one of said first and second means are emitted, the grid control circuit is blanked.

7. An apparatus as claimed in claim 5, further comprising;
   injector means for administrating an X-ray contrast medium into the object, the injection of the X-ray contrast medium being controlled by the system control means synchronously with the field synchronizing signals.

* * * * *